US005773835A

United States Patent [19]
Sinofsky

[11] Patent Number: 5,773,835
[45] Date of Patent: Jun. 30, 1998

[54] FIBER OPTIC SPECTROSCOPY

[75] Inventor: Edward L. Sinofsky, Dennis, Mass.

[73] Assignee: Rare Earth Medical, Inc., West Yarmouth, Mass.

[21] Appl. No.: 660,271

[22] Filed: Jun. 7, 1996

[51] Int. Cl.$^6$ .................................................. G01T 21/64
[52] U.S. Cl. .......................................................... 250/462.1
[58] Field of Search .......................... 250/462.1; 128/634

[56] References Cited

U.S. PATENT DOCUMENTS

| | | | |
|---|---|---|---|
| 3,335,715 | 8/1967 | Hugenholtz et al. | 128/634 |
| 3,498,286 | 3/1970 | Polanyi et al. | 128/634 |
| 4,233,493 | 11/1980 | Nath | 219/354 |
| 5,152,287 | 10/1992 | Kane | 128/634 |
| 5,421,337 | 6/1995 | Richards-Kortum et al. | 128/665 |
| 5,562,100 | 10/1996 | Kittrell et al. | 128/665 |

FOREIGN PATENT DOCUMENTS

| 0416931 | 3/1991 | European Pat. Off. | 128/634 |
|---|---|---|---|
| WO 96/07451 | 3/1996 | WIPO . | |

*Primary Examiner*—Constantine Hannaher
*Attorney, Agent, or Firm*—Thomas J. Engellenner; Lahive & Cockfield, LLP

[57] ABSTRACT

Methods and devices for practicing fluorescence spectroscopy to detect abnormal or cancerous tissue employing an transparent fluoropolymer optical probe to irradiate a target region of biological material and measure the fluorescent response of the target tissue. Based on the spectral response of the target region, the presence (or absence) of abnormal tissue can be determined. Transparent fluoropolymers reduce background fluorescence, thereby improving the signal-to-noise ratio in spectral analysis, because fluoropolymers have low self-fluorescence and, therefore, do not respond to ultraviolet excitation radiation with significant fluorescence of their own that would otherwise mask or interfere with the fluorescent radiation collected from a target tissue region in response to UV excitation radiation.

19 Claims, 4 Drawing Sheets

FIBER OPTIC SPECTROSCOPY

BACKGROUND OF THE INVENTION

The technical field of this invention is optical analysis of biological tissue and, in particular, the diagnosis of tissue samples and the differentiation of normal from abnormal tissue based on spectral analysis using optical fibers.

The endoscopic observation of biological tissue has become a very important tool in the detection and diagnosis of many diseases, including cancers. In particular, endoscopic diagnoses are increasingly common for gastrointestinal, colonic, and vaginal abnormalities.

Unfortunately, visual observations of biological tissue do not always permit the ready differentiation of normal and abnormal tissue structures. While biopsies can often be obtained for recognizable lesions, polyps, and the like, the identification of suitable sites for biopsy samples is also limited by the endoscope operator's visual acuity.

There exists the need for better tools for endoscopic detection of tissue diseases. In particular, devices which would either automatically detect the presence of abnormal tissues, or aid the clinician in visually identifying such abnormalities, would satisfy a long-felt need in the art.

SUMMARY OF THE INVENTION

Methods and devices are disclosed for practicing fluorescence spectroscopy to detect abnormal or cancerous tissue. In the present invention, a target region of biological material is irradiated with excitation radiation and the fluorescent response of the target tissue is measured. Based on the spectral response of the target region, the presence (or absence) of abnormal tissue can be determined. The present invention employs a transparent fluoropolymer to reduce background fluorescence, thereby improving the signal-to-noise ratio in spectral analysis.

It has been discovered that fluoropolymers have low self-fluorescence and, therefore, do not respond to ultraviolet excitation radiation with significant fluorescence of their own and, hence, they do not generate auto-fluorescent responses that mask or otherwise interfere with the fluorescent radiation that would be collected from a target tissue region in response to UV excitation radiation. Thus, fluoropolymer materials are particularly useful as windows, claddings, and sheath structures which surround a radiation-collecting, optical fiber and/or the source of excitation radiation.

In one embodiment of the invention, an apparatus for spectroscopic analysis is disclosed including a fiber optic excitation radiation source for irradiating a tissue region of biological material, at least one optical collection fiber, and a sheath surrounding at least part of the collection fiber, the sheath comprising a fluoropolymeric material that is substantially transparent to auto-fluorescent radiation emitted by the target region of tissue. In an alternative embodiment of the invention, the same fiber is used as both the excitation and collection means. In another embodiment, separate fibers are employed in the instrument to deliver excitation radiation and collect the fluorescent response. In yet a further embodiment of the invention, the excitation means can further include a reflective end cap and/or a diffuser element for emitting a circumferential, and axially uniform, pattern of light to the tissue surrounding a substantial portion of the instrument tip.

In another aspect of the invention, disposable sheaths are disclosed for encasing the optical elements of a fiber optic spectroscope. The fluoropolymer sheath surrounds the excitation and/or collection means of the instrument and provides a protective barrier which is transparent to both the UV excitation radiation and the fluorescent tissue response.

Suitable fluoropolymer materials include Teflon® materials in general, and, fluorinated ethylene-propylene copolymers (FEP) and perfluoroalkoxyethylene (PFA) materials.

A method according to the invention for detecting tissue abnormalities is also disclosed including the steps of irradiating a target region of biological material with excitation radiation, preferably in the ultraviolet region of the spectrum, and collecting fluorescent radiation from the target region through a fluoropolymer window material that is substantially transparent to the fluorescent radiation and which exhibits low self-fluorescence. The method further includes analysis of the fluorescent radiation from the target region in order to differentiate between normal and abnormal tissue.

The invention will next be described in connection with certain preferred embodiments. However, it should be clear to those skilled in the art that various additions, subtractions and other modifications can be made without departing from the spirit or scope of the invention.

DETAILED DESCRIPTION

Figure 1:
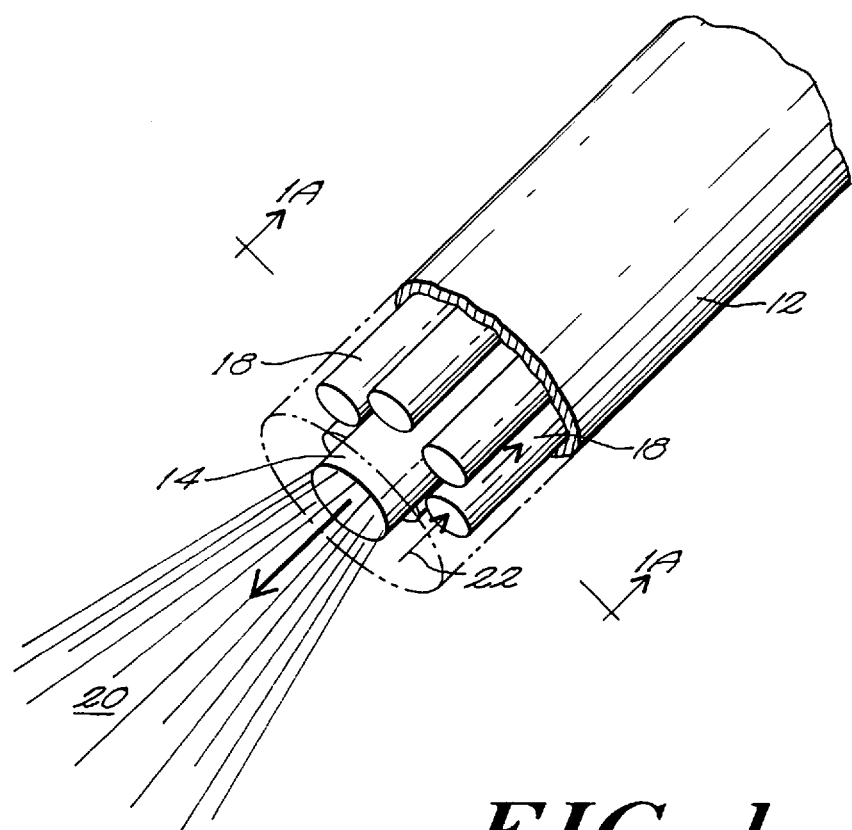
FIG. 1 is a schematic, partially cut away, perspective view of an apparatus for spectral analysis according to the invention.

In FIG. 1 an apparatus for spectroscopic analysis 10 is shown including a fluoropolymeric casing or sheath 12, an excitation fiber 14 through which radiation can be transmitted to the distal end 15 and emitted from the instrument as a conical pattern 20 of excitation radiation. The apparatus 10 further includes a number of collection fibers 18 which receive auto-fluorescent radiation 22 from the surrounding target region tissue. Although illustrated as optical fibers, it should be apparent that the collection means can be any light waveguide or assembly of optical elements, as known in the art, for collection of radiation from the target region.

Figure 1A:
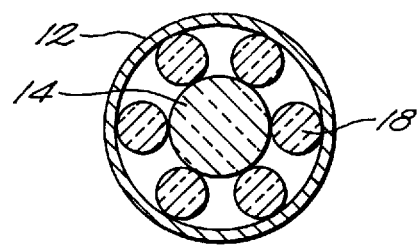
Fig. 1A is a cross-sectional view of the apparatus of FIG. 1 taken along section line A—A.

In Fig. 1A a cross-sectional view of the apparatus 10 of FIG. 1 is shown illustrating the placement of excitation fiber 14 and collection fibers 18, as well as the protective sheath 12. The sheath 12 is preferably formed of a fluoropolymer material having low self-fluorescence to yield low background fluorescence and, therefore, improve the signal-to-noise (S/N) ratio of the analysis. The fluoropolymer sheath or cladding 12 preferably is transparent to the excitation radiation source, which is typically ultraviolet radiation.

Unlike many polymeric materials and plastics which might be used as sheath materials or UV transparent windows, the fluoropolymer materials of the present invention do not absorb ultraviolet radiation and do not exhibit blue self-fluorescence which is typically characteristic of plastics, in general.

The sheath material 12 can also be disposable. Thus, it permits the clinician to reuse the optical elements 14 and 18 (as well as any other supporting structures) while ensuring that the instrument does not pass infectious agents from one patient to another. In practice, the clinician would remove the sheath following each procedure and replace it with a new disposable sheath before carrying out the next procedure.

The excitation fiber 14 can be any optic fiber that exhibits low fluorescence. For example, a 200-micrometer diameter fiber having a silica core and high OH content fiber with silica cladding. Similarly, the side fibers 18, which serve as the collection conduits for the tissue fluorescent signal, can also be high OH content, silica core fibers.

Figure 2:
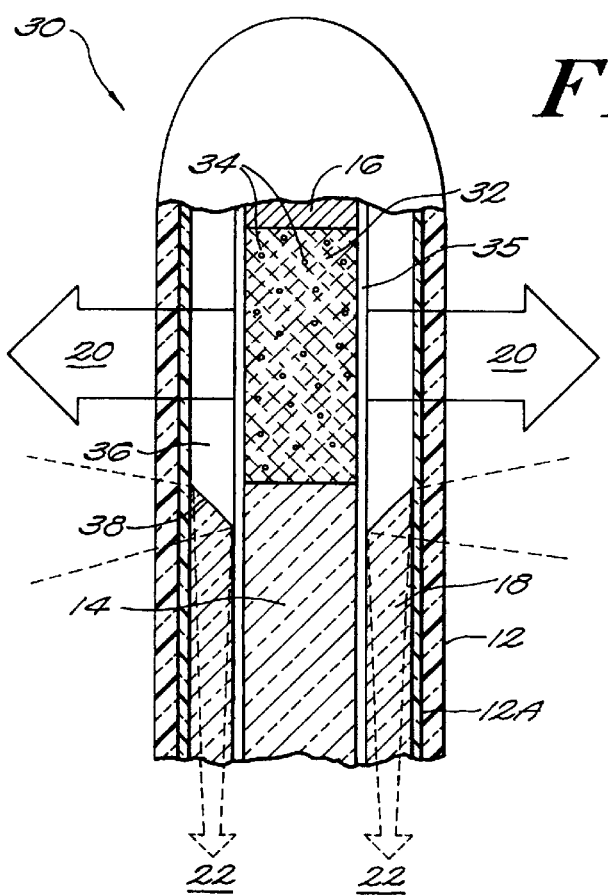
FIG. 2 is a partial, cross-sectional view of another apparatus for spectroscopic analysis according to the invention.

In FIG. 2 an alternative apparatus 30 is shown, again including excitation fiber 14, collection fibers 18, and outer sheath 12. In the embodiment of FIG. 2, the sheath element is divided into two parts: an inner layer 12A, also formed of a fluoropolymer, which serves to permanently encase the optical elements and an outer layer 12, which is a disposable sheath.

Furthermore, in FIG. 2, a diffuser element 32 is shown. Light transmitted via the excitation fiber 14 is directed into the diffuser 32 where a portion of the light will contact scatterers 34 and be scattered circumferentially outward in all directions. Light which is not scattered initially is reflected by end mirror 16 and passes through the scattering medium 32 again to create a diffuse pattern of excitation irradiation in the surrounding target tissue. The light-scattering diffuser 32 can be formed by embedding titania or alumina particles in a UV-transmitting, low fluorescence, epoxy which is disposed between the end of the fiber 14 and the mirror 16. In the illustrated embodiment, fiber 14 is joined to a tubular chamber 35 filled with the scattering medium 32. The other end of the tube is capped by end mirror 16. In addition, the embodiment of FIG. 2 shows collection fibers 18 having chamfered ends. These beveled surfaces 38 serves to redirect the fluorescent light 22 into the fiber 18 and back out of the instrument for spectrographic analysis.

Figure 3:
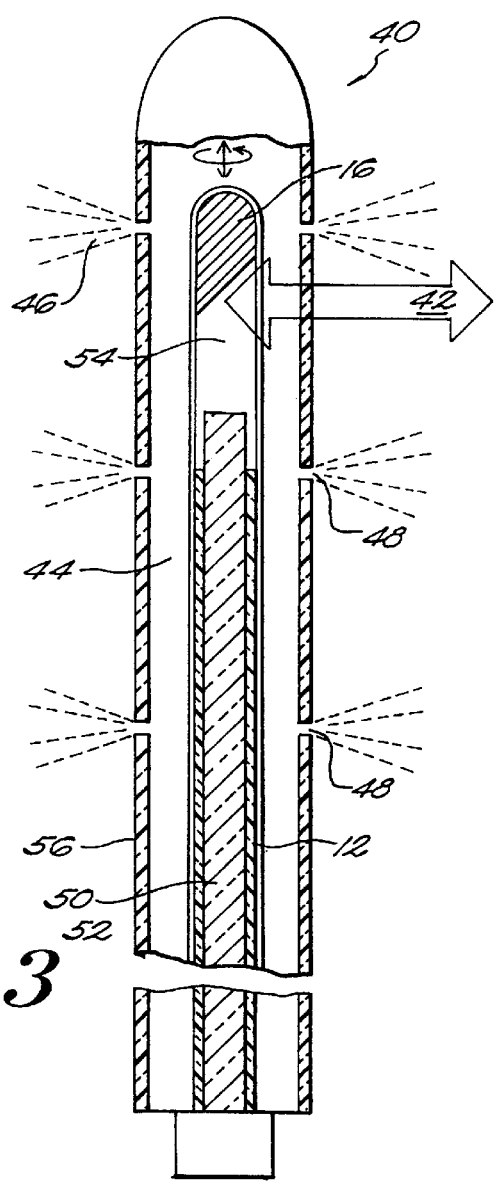
FIG. 3 is partially, cross-sectional view of another apparatus for spectroscopic analysis according to the invention.

In FIG. 3 another alternative apparatus 40 is shown including a single fiber 50 that serves as both the excitation and fluorescence collection medium. The fiber directs excitation light to an end mirror 16 for deflection sidewise out of the instrument. The double-headed arrow 42 is intended to illustrate the transmission of both excitation light out and the return of fluorescence back into the instrument 40.

As illustrated, the apparatus 40 includes a beveled mirror which directs excitation light in sideways direction. The instrument can further include drive means 78 for rotating the optical fiber to interrogate the tissue in a manner akin to a searchlight. Moreover, the optical fiber 50 can also be translated within the instrument by the drive means 78 for analysis at different axial locations. Again, chamber 54 can be empty or filled with a scattering composition such as that shown in FIG. 2.

The apparatus 40 of FIG. 3 also includes a disposable sheath 12 surrounding the optical elements. In addition, the apparatus 40 includes a second casement element 56 which surrounds the optical elements and provides a conduit 44 for the delivery of contrast agents 46, such as acetic acid, or dyes that enhance the responsive signal during endoscopic analysis. Both sheath 12 and casement 56 can be disposable elements and are preferably formed from fluoropolymer materials.

Figure 4:
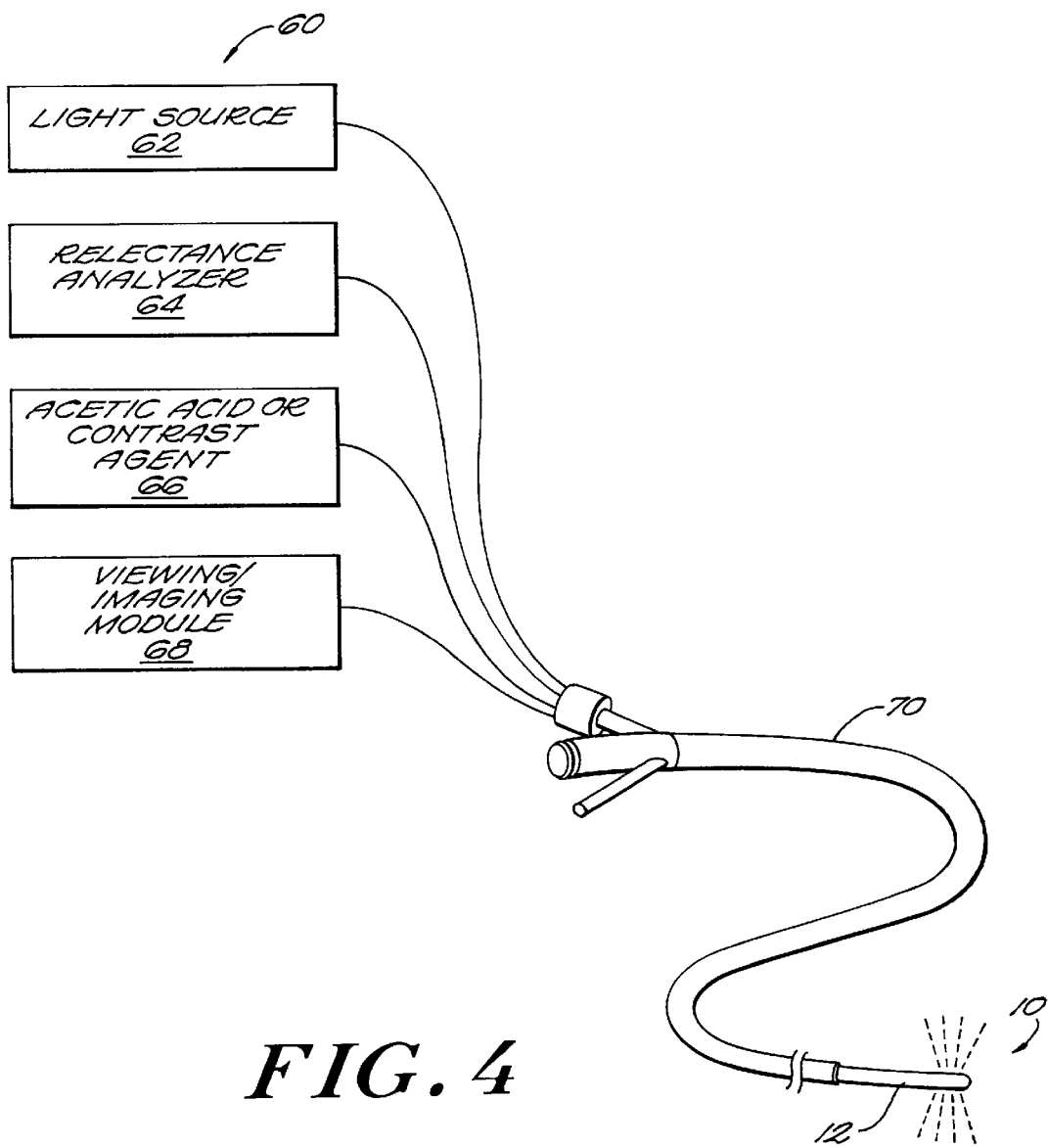
FIG. 4 is a schematic view of a system for spectroscopic analysis according to the invention.

In FIG. 4, a system 60 according to the present invention is disclosed for use with an endoscope 70. As shown, the apparatus for spectrographic analysis 10 including sheath 12, is introduced into the endoscope 70 and then positioned at a location within the patient where spectrographic data is desired. The apparatus can be coupled to a light source 62 which can be either a laser radiation source or simply a UV filtered lamp. One particularly useful radiation source is a nitrogen laser emitting excitation light at about 337 nanometers. However, the excitation light can be chosen from a wide region of the ultraviolet and/or visible spectrum. The excitation source can emit light of a wavelength ranging from about 250 nanometers to at least 600 nanometers, depending upon the application.

Also coupled to the system 60 of FIG. 4 is a fluorescence analyzer 64 which characterizes at least a portion of the light to detect auto-fluorescence and correlate such auto-fluorescence with known (or predicted) values of normal or diseased tissue.

The apparatus 60 of FIG. 4 can further include a contrast fluid source 66 for introducing contrast agents, such as acetic acid porphyrins or the like, into the endoscope to treat target regions prior to excitation and optical monitoring. The term "contrast agent" as used herein in intended to encompass any material that is taken up or which binds with a target tissue to enhance or otherwise modify the optical properties of the target tissue. Acetic acid, for example, is known to cause many types of neoplastic and dysplastic tissue to turn white and, thus, be more readily identified under visual observation. Finally, the system can include imaging optics 68 for viewing or recording images of the target tissue and/or observed fluorescence and for recording a permanent image of the tissue structures.

Figure 5A:
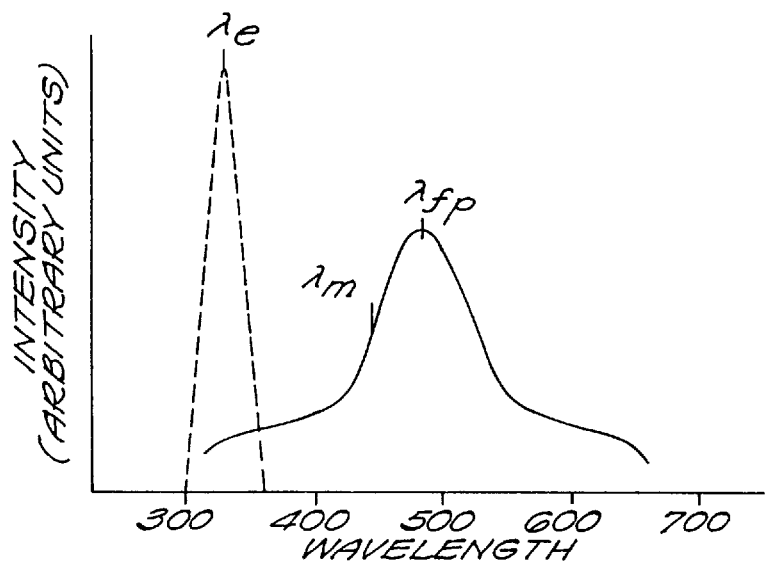
FIG. 5A is graph of intensity in arbitrary units versus wavelength for an excitation signal and an idealized response signal from normal tissue.
Figure 5B:
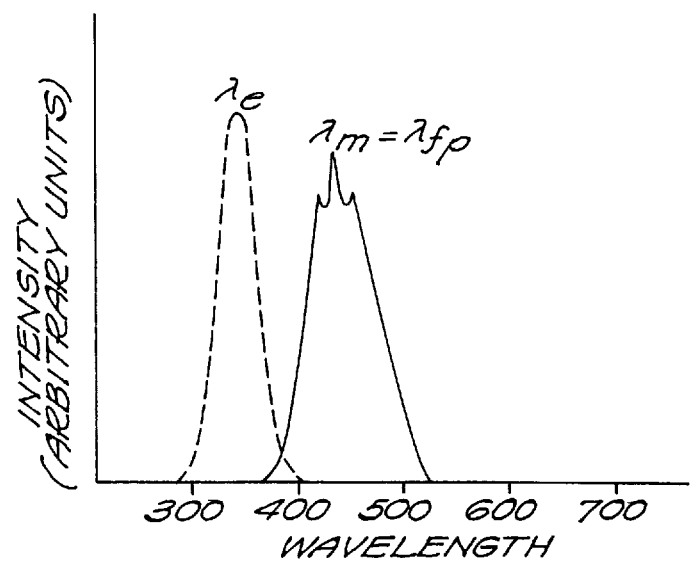
FIG. 5B is a graph of intensity (again in arbitrary units) versus wavelength of excitation radiation and an idealized response from a diseased tissue sample.

In FIGS. 5A and 5B, a spectral analysis according to the present invention is illustrated. It is known that certain diseased tissues exhibit different fluorescent signatures than healthy tissue. This is illustrated schematically by the response curves in FIGS. 5A and 5B. As shown in FIG. 5A, the excitation light has a peak $\lambda_e$ at about 337 nanometers. The healthy tissue response of FIG. 5A shows a peak fluorescence of about 470 nanometers. An indicator wavelength $\lambda_m$ of 440 can be chosen for monitoring purposes.

In FIG. 5B a similar graph is illustrated for an idealized specimen of diseased tissue (e.g., a cancerous polyp of the colon). In the graph of FIG. 5B the fluorescent response has shifted to a lower wavelength and it is now centered at about the indicator wavelength $\lambda_m$.

Accordingly, a simple spectral analyzer can take ratios of $\lambda_e$ to $\lambda_m$ for tissue samples and based on the ratio values make predictions as to the state of target tissue specimens. While this methodology has been described in very simple form with a simple idealized curve and one ratio measurement, it should be clear that more comprehensive monitoring of the fluorescent spectrum can also be conducted and would indeed be desirable in a commercial instrument. Nonetheless, the principles illustrated above would be simply followed with repeated measurements of different ratios based on known empirical data.

What is claimed is:

1. An apparatus for spectral analysis comprising excitation means for irradiating a target region of a biological material with excitation radiation;

collection means for collecting fluorescent radiation from the target region that is emitted in response to said excitation radiation; and a casing surrounding at least a portion of the collection means, the casing comprising a fluoropolymer material that exhibits low auto fluorescence and is substantially transparent to fluorescent radiation emitted by the target region.

2. The apparatus of claim 1 wherein the fluoropolymer casing is a disposable sheath.

3. The apparatus of claim 1 wherein the casing surrounds at least part of both the excitation means and the collection means.

4. The apparatus of claim 1 wherein the excitation means comprises at least one optical fiber.

5. The apparatus of claim 4 wherein the excitation means further includes a reflective end cap to reflect light from the optical fiber towards a target region.

6. The apparatus of claim 1 wherein the excitation means further comprises a source of radiation.

7. The apparatus of claim 6 wherein the source of radiation is a laser.

8. The apparatus of claim 6 wherein the source of radiation is a UV-filtered lamp.

9. The apparatus of claim 6 wherein the source of radiation is a source of radiation emitting radiation at a wavelength ranging from about 200 to about 600 nanometers.

10. The apparatus of claim 1 wherein the excitation means further includes a diffuser element to diffuse radiation from the excitation means to the surrounding tissue region.

11. The apparatus of claim 1 wherein the collection means further comprises at least one optical fiber.

12. The apparatus of claim 1 wherein the collection means further comprises a plurality of optical fibers.

13. The apparatus of claim 1 wherein the apparatus further comprises an outer sheath, surrounding said casing.

14. The apparatus of claim 13 wherein the apparatus further includes at least one passageway between said casing and said outer sheath for the delivery of fluids to the target region.

15. The apparatus of claim 1 wherein the casing is coupled to the collection means such that at least part of the collection means is capable of rotation.

16. The apparatus of claim 1 wherein the casing is coupled to the collection means such that at least part of the collection means is capable of translation.

17. A method of analyzing biological material comprising:

irradiating a target region of a biological material with excitation radiation from at least one light-transmitting excitation fiber;

collecting fluorescent radiation from the target region via at least one optical collection fiber encased in a fluoropolymer casing that exhibits low auto fluorescence and which is substantially transparent to fluorescent radiation emitted by the target region; and analyzing the collected radiation from the target region to characterize the biological material.

18. The method of claim 17 wherein the step of irradiating the target region further comprises irradiating the target region with ultraviolet radiation.

19. The method of claim 17 wherein the method further comprises encasing both the excitation fiber and the collection fiber in a disposable fluoropolymer sheath.

* * * * *